United States Patent [19]

Linn et al.

[11] Patent Number: 5,800,989
[45] Date of Patent: Sep. 1, 1998

[54] METHOD FOR DETECTION OF NUCLEIC ACID TARGETS BY AMPLIFICATION AND FLUORESCENCE POLARIZATION

[75] Inventors: Carl Preston Linn, Durham; G. Terrance Walker, Chapel Hill; Patricia Anne Spears, Raleigh, all of N.C.

[73] Assignee: Becton, Dickinson and Company, Franklin Lakes, N.J.

[21] Appl. No.: 559,010

[22] Filed: Nov. 15, 1995

[51] Int. Cl.$^6$ .............................. C12Q 1/68; C12P 19/34
[52] U.S. Cl. .................. 435/6; 435/91.21; 435/91.2
[58] Field of Search .................. 435/91.2, 91.21, 435/6

[56] References Cited

U.S. PATENT DOCUMENTS

| | | | |
|---|---|---|---|
| 5,232,829 | 8/1993 | Longiaru et al. | 435/6 |
| 5,270,184 | 12/1993 | Walker et al. | 435/91.2 |
| 5,455,166 | 10/1995 | Walker | 435/91.2 |
| 5,593,867 | 1/1997 | Walker et al. | 435/91.2 |

FOREIGN PATENT DOCUMENTS

| | | |
|---|---|---|
| 0 382 433 | 2/1989 | European Pat. Off. . |
| 0 678 581 | 10/1995 | European Pat. Off. . |
| 0 678 582 | 10/1995 | European Pat. Off. . |
| 2 228 998 | 4/1993 | United Kingdom . |
| WO 92/18650 | 10/1992 | WIPO . |

OTHER PUBLICATIONS

Wright, D.J. et al. (May 1995) Abstracts 95th Gen. Mtg. Am. Soc. Microbiol. 95(0): 133.

G. T. Walker, et al. "Isothermal in vitro amplification of DNA by a restriction enzyme/DNA polymerase system" *Proc. Natl. Acad. Sci. USA* 89, 392–396 (1992).

G. T. Walker, et al. "Strand displacement amplification—an isothermal, in vitro DNA amplification technique" *Nucl. Acids Res.* 20, 1691–1696 (1992).

A. Murakami, et al. "Fluorescent-labeled oligonucleotide probes: detection of ohybrid formation in solution by fluorescence polarization spectroscopy" *Nucl. Acids Res.* 19, 4097–4102 (1991).

*Primary Examiner*—Lisa B. Arthur
*Attorney, Agent, or Firm*—Donna R. Fugit

[57] ABSTRACT

Fluorescence polarization methods for detection of nucleic acid amplification at thermophilic temperatures employ a fluorescently labeled oligonucleotide signal primer which is converted from single- to double-stranded form in a target amplification-dependent manner. This conformational change is accompanied by an increase in fluorescence polarization values. The decrease in FP typically observed for the duplex at elevated temperatures is overcome by double-stranded DNA binding proteins which are believed to stabilize the double-stranded structure by reducing the single-strandedness normally associated with higher temperatures. The inventive methods provide a closed, homogeneous system for amplification and detection of amplification in real-time or at an endpoint.

20 Claims, 2 Drawing Sheets

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:1:

ATCCGTATGG TGGATAACGT CTTTCA                 26

( 2 ) INFORMATION FOR SEQ ID NO:2:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:2:

CGATTCCGCT CCAGACTTCT CGGGTCTACT GAGATCCCCT       40

( 2 ) INFORMATION FOR SEQ ID NO:3:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:3:

ACCGCATCGA ATGCATCTCT CGGGTAAGGC GTACTCGACC       40

( 2 ) INFORMATION FOR SEQ ID NO:4:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

CGCTGAACCG GAT                                                                  13

( 2 ) INFORMATION FOR SEQ ID NO:5:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:5:

TCCACCCGCC AAC                                                                  13

METHOD FOR DETECTION OF NUCLEIC ACID TARGETS BY AMPLIFICATION AND FLUORESCENCE POLARIZATION

FIELD OF THE INVENTION

The present invention relates to methods for detecting amplification of nucleic acid target sequences and in particular to detection of amplification by fluorescence polarization.

BACKGROUND OF THE INVENTION

Fluoresence Polarization (FP) is a measure of the time-average rotational motion of fluorescent molecules. It has been known since the 1920's and has been used in both research and clinical applications for sensitive determination of molecular volume and microviscosity. The FP technique relies upon changes in the rotational properties of molecules in solution. That is, molecules in solution tend to "tumble" about their various axes. Larger molecules (e.g., those with greater volume or molecular weight) tumble more slowly and along fewer axes than smaller molecules. There is therefore less movement between excitation and emission, causing the emitted light to exhibit a relatively higher degree of polarization. Conversely, fluorescence emissions from smaller fluorescent molecules, which exhibit more tumbling between excitation and emission, are more multiplanar (less polarized). When a smaller fluorescent molecule takes a larger or more rigid conformation its tumbling decreases and the emitted fluorescence becomes relatively more polarized. This change in the degree of polarization of emitted fluorescence can be measured and used as an indicator of increased size and/or rigidity of the fluorescent molecule.

In fluorescence polarization techniques, the fluorescent molecule is first excited by polarized light. The polarization of the emission is measured by measuring the relative intensities of emission (i) parallel to the plane of polarized excitation light and (ii) perpendicular to the plane of polarized excitation light. A change in the rate of tumbling due to a change in size and/or rigidity is accompanied by a change in the relationship between the plane of excitation light and the plane of emitted fluorescence, i.e., a change in fluorescence polarization. Such changes can occur, for example, when a single stranded oligonucleotide probe becomes double stranded or when a nucleic acid binding protein binds to an oligonucleotide. Fluorescence anisotropy is closely related to FP. This technique also measures changes in the tumbling rates of molecules but is calculated using a different equation. It is to be understood that polarization and anisotropy are interchangeable techniques for use in the present invention. The term fluorescence polarization is generally used herein but should be understood to include fluorescence anisotropy methods. In steady state measurements of polarization and anisotropy, these values are calculated according to the following equations:

$$P(\text{polarization}) = \frac{Ipa - Ipe}{Ipa + Ipe}$$

$$r(\text{anisotropy}) = \frac{Ipa - Ipe}{Ipa + 2Ipe}$$

where Ipa is the intensity of fluorescence emission parallel to the plane of polarized excitation light and Ipe is the intensity of fluorescence emission perpendicular to the plane of polarized excitation light.

As FP is homogenous, this technique is ideal for studying molecular interactions in solution without interference by physical manipulation. Fluorescence polarization is therefore a convenient method for monitoring conversion of single-stranded fluorescently labelled DNA to double-stranded form by hybridization (Murakami, et al. 1991. *Nucl. Acids Res.* 19, 4097–4102). The ability of FP to differentiate between single and double-stranded nucleic acid conformations without physical separation of the two forms has made this technology an attractive alternative for monitoring probe hybridization in diagnostic formats. European Patent Publication No. 0 382 433 describes fluorescence polarization detection of amplified target sequences by hybridization of a fluorescent probe to the amplicons or by incorporation of a fluorescent label into the amplification products by target-specific extension of a fluorescently-labeled amplification primer. PCT Patent Publication No. WO 92/18650 describes similar methods for detecting amplified RNA or DNA target sequences by the increase in fluorescence polarization associated with hybridization of a fluorescent probe.

Fluorescence polarization may be monitored as either transient state FP or steady state FP. In transient state FP, the excitation light source is flashed on the sample and polarization of the emitted light is monitored by turning on the photomultiplier tube after the excitation light source is turned off. This reduces interference from light scatter, as fluorescence lasts longer than light scatter, but some fluorescence intensity is lost. In steady state FP, excitation light and emission monitoring are continuous (i.e., the excitation source and photomultiplier tube are on continuously). This results in measurement of an average tumbling time over the monitoring period and includes the effects of scattered light.

In vitro and in situ nucleic acid amplification techniques have provided extremely sensitive tools for detection and analysis of small amounts of nucleic acids. Nucleic acid amplification techniques can be grouped according to the temperature requirements of the procedure. The polymerase chain reaction (PCR; R. K. Saiki, et al. 1985. *Science* 230, 1350-1354), ligase chain reaction (LCR; D. Y. Wu, et al. 1989. *Genomics* 4, 560–569; K. Barringer, et al. 1990. *Gene* 89, 117–122; F. Barany. 1991. *Proc. Natl. Acad Sci. USA* 88, 189–193) and transcription-based amplification (D. Y. Kwoh, et al. 1989. *Proc. Natl. Acad Sci. USA* 86, 1173–1177) require temperature cycling. In contrast, methods such as Strand Displacement Amplification (SDA; G. T. Walker, et al. 1992. *Proc. Natl. Acad Sci. USA* 89, 392–396 and G. T. Walker, et al. 1992. *Nuc. Acids. Res.* 20, 1691–1696, and U.S. Pat. No. 5,455,166), self-sustained sequence replication (3SR; J. C. Guatelli, et al. 1990. *Proc. Natl. Acad. Sci USA* 87, 1874–1878), Nucleic Acid Sequence Based Amplification (U.S. Pat. No. No. 5,409,818), restriction amplification (U.S. Pat. No. 5,102,784) and the Qβ replicase system (P. M. Lizardi, et al. 1988. *Bio-Technology* 6, 1197–1202) are isothermal reactions. Isothermal amplifications are conducted at essentially constant temperature, in contrast to the cycling between high and low temperatures characteristic of amplification reactions such as the PCR.

Strand Displacement Amplification (SDA) utilizes nicking of a hemimodified restriction endonuclease recognition site by a restriction enzyme and displacement of a downstream DNA strand by a polymerase to amplify a target nucleic acid (U.S. Pat. No. 5,270,184, Walker, et al. 1992. *Proc. Natl. Acad Sci. USA* 89, 392–396; Walker, et al. 1992. *Nucl. Acids Res.* 20, 1691–1696). The SDA reaction originally reported in the publications cited above ("conventional SDA") is typically conducted at a temperature between about 35° C. and 45° C., and is capable of $10^8$-fold amplification of a target sequence in about 2 hours. Recently, SDA has been adapted for higher reaction temperatures (about 45°–65° C.—"thermophilic SDA" or "tSDA"). tSDA is capable of producing $10^9$–$10^{10}$ fold amplification in about 15–30 min. at about 50°–60° C. In addition to increased reaction speed, there is a significant reduction in non-specific background amplification in tSDA as compared to conventional SDA.

Typically, amplified target sequences are detected by post-amplification hybridization of probes. This requires separation of free and hybridized probe before the signal can be measured. However, monitoring changes in FP allows differentiation of free and hybridized probe without physical separation and therefore enables amplification and detection of amplification in a homogeneous, closed system. A closed, homogeneous assay reduces operating steps and procedural complexity, as well as providing improved control of the dispersal of amplification products in the laboratory, thereby reducing the potential for false positives due to accidental contamination of samples with target DNA. FP detection has been applied to detection of amplification in methods in which double-stranded secondary amplification products are generated during the amplification reaction from a single-stranded signal primer comprising a fluorescent label. Generation of secondary amplification products during target amplification is described and illustrated in published European Patent Application Nos. 0 678 582 and 0 678 581. In the process, a single-stranded oligonucleotide signal primer comprising a detectable label is converted to double-stranded form in a target amplification-dependent manner. Hybridization, extension and displacement of the signal primer occurs concurrently with the amplification reaction. When the label is fluorescent, conversion of the signal primer to double-stranded form may be detected as a change in FP. Conversion of the signal primer to double-stranded form results in an increase in FP of approximately 20 mP using fluorescein or La Jolla Blue as the fluorescent label. This change in FP can be enhanced (e.g., to about 133–185 mP) by binding a double-stranded DNA binding protein to its specific binding sequence present in the secondary amplification product. Enhancement is therefore amplification-specific because protein binding can only occur once the binding sequence in the secondary amplification product becomes double-stranded as a result of target amplification.

The speed and specificity of target amplification is increased at higher reaction temperatures (typically about 45°–75° C.). It is therefore desirable to combine the advantages of FP for detecting amplification with elevated amplification temperatures. However, increased reaction temperatures were predicted to be incompatible with measurement of fluorescence polarization. Many fluorescent labels are not stable at higher temperatures. In addition, higher temperatures promote "breathing" of the duplex and "fraying" of the ends, leading to increased single-strandedness. Increased single-strandedness near the fluorescent label, particularly at the ends of the duplex, could result in significant decreases in FP for the double-stranded form, potentially eliminating any amplification-associated increase in FP under these reaction conditions. These concerns were supported by preliminary experiments evaluating FP at 55° C. At this temperature (which is a typical reaction temperature for tSDA), there was no difference in FP between the single-stranded and double-stranded forms of oligonucleotides. Further, FP is sensitive to sample viscosity, which is altered at higher temperatures. The effects of altered sample viscosity on the ability to use changes in FP for detection of amplification at increased reaction temperatures were therefore uncertain.

The following terms are defined herein as follows:

An amplification primer is a primer for amplification of a target sequence by hybridization and extension of the primer. For SDA, the 3' end of the amplification primer is a target binding sequence which hybridizes at the 3' end of the target sequence. The amplification primer further comprises a recognition site for a restriction endonuclease 5' to the target binding sequence, generally near its 5' end. The restriction endonuclease recognition site is a nucleotide sequence recognized by a restriction endonuclease which will nick a double stranded recognition site for the restriction endonuclease when the recognition site is hemimodified, as described by Walker, et al. (1992a), supra. For amplification methods which do not require specialized sequences at the ends of the target, the amplification primer generally consists essentially of only the target binding sequence. Amplification methods which require specialized, non-target binding sequences other than the nickable restriction endonuclease recognition site of SDA (e.g., 3SR) may employ amplification primers comprising a target binding sequence and the sequence or structure required by the selected amplification method.

The terms target or target sequence refer to nucleic acid sequences (DNA and/or RNA) to be amplified. These include the original nucleic acid sequence to be amplified and its complementary second strand as well as copies of either strand of the original target sequence produced during amplification. These copies also serve as amplifiable target sequences by virtue of the fact that they contain copies of the original target sequences to which the amplification primers hybridize.

Amplification products or amplicons are oligo or polynucleotides which comprise copies of the target sequence produced during amplification of the target sequence.

A signal primer hybridizes to the target sequence downstream of an amplification primer and is extended by polymerase in a manner similar to extension of the amplification primer. A signal primer may also be referred to as a detector probe. Extension of the amplification primer displaces the downstream, extended signal primer from the target sequence. The opposite amplification primer then hybridizes to the extended, displaced signal primer and is extended by polymerase, resulting in incorporation of the signal primer into a longer duplex indicative of target amplification (the secondary amplification product). The secondary amplification products comprise an internal segment of the amplification product and a detectable label which is associated with the signal primer.

SUMMARY OF THE INVENTION

The present invention provides methods using FP and a signal primer comprising a fluorescent label for detection of nucleic acid amplification at elevated temperatures (thermophilic amplification, e.g., at about 45°–75° C.). Amplification is detected as an increase in FP associated with target amplification-dependent generation of double-stranded, fluorescent secondary amplification products from the single-stranded signal primer. Although preliminary experiments indicated that the increased single-strandedness of the secondary amplification products at higher temperatures would severely reduce or eliminate the increase in FP associated with target amplification, it was unexpectedly found that under the conditions of thermophilic target amplification the increase in FP is maintained. This phenomenon appears to be due to binding of the double-stranded DNA binding proteins in the amplification reaction to the double-stranded secondary amplification product, resulting in stabilization of the double-stranded form. Further, it has been found that when the target is amplified in a thermophilic amplification reaction, sequence non-specific double-stranded DNA binding proteins such as the amplification polymerase can enhance the change in fluorescence polarization associated with target amplification-dependent generation of secondary amplification products, regardless of whether fluorescence polarization is measured at low temperatures (less than about 45° C.) or at thermophilic temperatures (about 45°–75° C.).

DETAILED DESCRIPTION OF THE INVENTION

Recently developed methods for detection of amplification employ at least one signal primer. The signal primer is included in the amplification reaction to facilitate detection or monitoring of target amplification. During target amplification the signal primer is extended and rendered double-stranded as a result of target amplification to produce a secondary amplification product (EP 0 678 582 and EP 0 678 581). Conversion of the single-stranded signal primer to double-stranded form in the secondary amplification product is an indication of target amplification, as secondary amplification products are not produced in the absence of target amplification. Single- to double-stranded conversion of the signal primer may be monitored by measuring fluorescence polarization or fluorescence anisotropy when the label of the signal primer is fluorescent. That is, the decrease in the local mobility of the fluorophore resulting from the change in probe conformation (primarily strandedness) results in a detectable change in correlation time (tumbling time) for the fluorescent label. The accompanying changes in FP values may be monitored on a transient-state fluorometer (e.g., from Diatron) or a steady state fluorometer (e.g., Jolley Instruments) appropriate for detection of the selected fluorescent label. Fluorescence polarization measurements may be taken post-amplification (endpoint measurement) or concurrently with the amplification reaction (real-time measurement). Real-time monitoring of fluorescence provides significant advantages in the assay. That is, it provides an essentially immediate result, it is quantitative, it improves sensitivity (analysis of a change in slope is more accurate than a single endpoint), and the sample acts as its own internal standard. This last advantage is particularly important for analysis of clinical specimens, as sample viscosity may significantly affect endpoint readings.

As the hybridized and unhybridized (i.e., double- and single-stranded) signal primers are not separated prior to measurement, FP-based detection of target amplification requires appreciable conversion of the single-stranded fluorescent signal primer to double-stranded form. Therefore, lower signal primer concentrations facilitate high sensitivity (ie., detection of amplification of initially low concentrations of target sequence) because they result in a higher percentage of converted signal primer for a given level of target amplification. However, low signal primer concentrations present a kinetic challenge for the amplification reaction. The fluorescent signal primer must hybridize to the target strand before hybridization and extension of the upstream amplification primer. It is therefore generally advantageous to adjust the relative primer concentrations such that the signal primer is at a lower concentration than the amplification primer which displaces it, and the signal primer displacing amplification primer is at a lower concentration than the amplification primer which is not displacing a signal primer.

The processes illustrated in EP 0 678 582 and EP 0 678 581 occur concurrently with the amplification reaction and do not interfere with it. In SDA, any mispriming by the signal primer and an amplification primer generates an extension product which cannot be exponentially amplified due to the presence of only one nickable restriction endonuclease recognition site (i.e., the fluorescent signal primer does not contain a nickable restriction endonuclease recognition site). Non-specific increases in FP due to signal primer mispriming are therefore negligible, as SDA requires two primers (each containing a nickable restriction endonuclease recognition site) to support exponential amplification. This is in contrast to the Polymerase Chain Reaction, in which any extendible oligonucleotide which hybridizes can serve as an amplification primer, allowing misprimed products to be exponentially amplified. Background from mispriming by the signal primer is further reduced when the signal primer is present at low concentrations (e.g., 50 pM–20 nM). Reduced signal primer concentration and their inability to function as amplification primers probably make a relatively large contribution to the reduction of non-specific background due to signal primer mispriming in conventional SDA. However, because the increased reaction temperatures of tSDA typically result in significantly lower levels of mispriming than in conventional SDA, the effect of signal primer concentration and structure are difficult to assess in this system.

At typical temperatures for isothermal nucleic acid amplification (e.g., 35°–42° C.) the conversion of 5' fluorescein-labeled signal primer from single-stranded to double-stranded form produces an easily detectable increase in FP of about 20 mP. This increase can be enhanced by addition of a sequence-specific double-stranded DNA binding protein such as a restriction endonuclease, repressor protein, receptor binding protein, etc. By incorporating the appropriate recognition site for the double-stranded DNA binding protein into the signal primer, the recognition site becomes double-stranded as a result of target amplification, allowing amplification-specific binding of the protein and enhancement of the change in FP. At lower temperatures specific protein binding sequences are necessary to ensure protein binding exclusively to secondary amplification products. This is believed to be due to the relatively high levels of non-specific priming at lower temperatures. Without specific recognition sequences, it is believed that the double-stranded DNA binding protein binds to non-specific background amplification products in sufficient amounts to eliminate any amplification-specific enhancement of the change in FP.

Preliminary experiments suggested that the increase in FP associated with generation of secondary amplification products would decrease with increasing temperature for end-labeled signal primers, and that it would be substantially eliminated at the reaction temperatures typical of thermophilic amplification reactions such as PCR and tSDA. In nucleic acid hybridization studies, the change in FP (ΔmP) was substantially unaffected at temperatures below about 45° C. However, ΔmP began to decrease at about 45° C. and was essentially absent as hybridization temperatures approached about 60° C. However, it was unexpectedly found that the change in FP could be maintained when generation of secondary amplification products was monitored in thermophilic amplification reactions in the temperature range at which FP values were negatively affected in hybridization studies, e.g., about 45°–75° C. As the polymerases used to amplify nucleic acid targets are double-stranded nucleic acid binding proteins, Applicants believe that this phenomenon is due to sequence-nonspecific binding of the amplification polymerase to the secondary amplification products. Binding of the polymerase may contribute to stabilization of the duplex and reduction or elimination of the increased single-strandedness associated with higher hybridization temperatures. This results in a target-amplification specific increase in FP which would not be predicted from simple hybridization experiments conducted at similar temperatures.

In addition, it was unexpectedly found that amplification at higher temperatures permits the use of sequence non-specific double-stranded DNA binding proteins for enhancement of amplification-associated changes in FP. Conventional SDA, in contrast to tSDA, did not exhibit any enhancement of FP in the presence of the sequence-nonspecific DNA binding proteins in the amplification reaction. The different results in these two amplification systems may be due to the increased amount of nonspecific background amplification product produced by conventional SDA. These double-stranded background amplicons could prevent detection of enhancement of the change in FP by binding substantial amounts of any sequence non-specific double-stranded DNA binding protein which may be present. The substantial absence of background amplification in tSDA may therefore allow detection of enhanced changes in FP by ensuring that the sequence non-specific double-stranded DNA binding protein is primarily bound by secondary amplification products. FP detection of amplification in thermophilic amplification systems is therefore significantly simplified, as there is no need to engineer specific binding sequences into the signal primer and the requirement for an additional reaction component (a separate double-stranded DNA binding protein) is eliminated. That is, the enzymes already present for target amplification (e.g., polymerase) stabilize the double-stranded secondary amplification product to maintain the change in FP at higher temperatures and may also serve to enhance the increase in FP which indicates target amplification. That is, under the reaction conditions of thermophilic amplification, the FP increase is maintained at levels at least comparable to those observed at about 37° C., except for minor changes in magnitude due changes in sample viscosity.

The Strand Displacement Amplification target generation and amplification reaction schemes are illustrated in Walker, et al., supra, U.S. Pat. No. 5,455,166 and U.S. Pat. No. 5,270,184. These general reaction schemes are the same for both conventional SDA and tSDA. However, tSDA employs thermostable restriction endonucleases and polymerases and is conducted at higher temperatures. SDA requires a polymerase which lacks 5'–3' exonuclease activity, initiates polymerization at a single stranded nick in double stranded nucleic acids, and displaces the strand downstream of the nick while generating a new complementary strand using the un-nicked strand as a template. Displacement activity is essential to the amplification reaction, as it makes the target available for synthesis of additional copies and generates the single-stranded extension product to which a second amplification primer may hybridize in exponential amplification reactions. Examples of polymerases which are thermostable and have the other characteristics required for use in tSDA are exo⁻ Vent (New England BioLabs), exo⁻ Deep Vent (New England BioLabs), Bst (BioRad), exo⁻ Pfu (Stratagene), Bca (Panvera) and Sequencing Grade Taq (Promega). Others may be identified using routine screening assays. The polymerases Tth (Boehringer), Tfl (Epicentre), REPLINASE (DuPont) and REPLITHERM (Epicentre) strand displace from a nick, but also have 5'–3' exonuclease activity. These polymerases are useful in tSDA after removal of the exonuclease activity, e.g., by genetic engineering. Most of the thermophilic polymerasees identified so far have optimal activity at 65°–76° C. However, as the thermostability of thermophilic restriction endonucleases is generally limited to less than about 65° C., thermophilic polymerases with optimal activity at lower temperatures (e.g., Bst and Bca) are more compatible with thermophilic restriction endonucleases for use in tSDA.

Nicking by the restriction endonuclease perpetuates the SDA reaction, allowing subsequent rounds of target amplification to initiate. Because restriction enzymes generally produce double strand breaks, cleavage of one of the two strands in the duplex of the cleavage site must be selectively inhibited. This is usually accomplished by introducing nucleotide analogs (e.g., deoxynucleoside phosphorothioates) into one strand of the DNA during synthesis so that one of the two strands is no longer susceptible to cleavage. Examples of restriction endonucleases suitable for use in tSDA include BsrI, BstNI, BsmAI, BslI and BsoBI (New England BioLabs), and BstOI (Promega). Others may be identified in routine screening assays to identify nicking activity at the temperatures of tSDA.

The present disclosure uses tSDA as an example of thermophilic amplification, however, the invention may also be applied to any amplification method in which a strand-displacing polymerase is used or in which a strand-displacing polymerase can be substituted for a polymerase which has 5'–3' exonuclease activity to displace a downstream signal primer. The inventive methods may therefore be used in isothermal amplification reactions other than SDA, e.g., Self-Sustained Sequence Replication (3SR), as the detection method is independent of whether the target sequence is RNA or DNA. In 3 SR, target-dependent generation of double-stranded signal primer occurs generally as it does for SDA. The T7 RNA polymerase used in 3SR lacks 5'–3' exonuclease activity and the degradative activity of reverse transcriptase is an RNAse H activity which is active only on RNA hybridized to DNA. Therefore, in the 3SR amplification scheme of Guatelli, et al. (1990. 87, 1874–1878), the signal primer may hybridize to the RNA target sequence and be displaced by extension of the 3' amplification primer ("A" in FIG. 1 of Guatelli, et al.). Alternatively, the signal primer may hybridize to the cDNA target sequence generated by reverse transcription in the 3 SR reaction. In either case, the extended signal primer is displaced by the polymerase when the upstream 3' ("A") or 5' ("B") amplification primer is extended. The opposite amplification primer then binds to the signal primer extension product and is extended, converting the labeled signal primer to double-stranded form. The Transcription Mediated Amplification (TMA) and Nucleic Acid Sequence Based Amplification (NASBA) reactions are essentially the same as 3SR and would perform similarly to produce double-stranded target amplification-specific secondary amplification products with addition of a signal primer. Although 3 SR and related amplification methods are currently conducted at temperatures below the thermophilic temperature range (i.e., less than about 45°–75° C.), substitution of thermostable enzymes as necessary should allow fluorescence polarization detection of amplification under thermophilic conditions according to the present invention, as all of these amplification reactions include a sequence non-specific double-stranded DNA binding protein which would stabilize duplexes and maintain FP changes at the higher temperatures.

The inventive methods may also be applied to detecting amplification in the Polymerase Chain Reaction (PCR), although fluorescence polarization measurements must be taken during the lower temperature periods of the amplification cycle for "real time" monitoring of amplification. Primer hybridization and extension in PCR are typically conducted at reduced but still thermophilic temperatures (about 60°–75° C.). Using a 5'–3' exonuclease deficient polymerase (e.g., exo⁻ Vent, exo⁻ Pfu, or the Stoffel fragment of Taq), extension of a PCR amplification primer hybridized to the target sequence displaces the extended downstream signal primer. The opposite PCR amplification primer hybridizes to the extension product of the signal primer and is extended, resulting in conversion of the single-stranded signal primer to double-stranded form. The double-stranded signal primer is amplifiable by hybridization and extension of one amplification primer and one signal primer in subsequent cycles, providing an additional source of double-stranded signal primer. The increase in fluorescence polarization or fluorescence anisotropy may then be detected after conclusion of the PCR under conditions in which amplification products remain double-stranded (below about 45° C.). Alternatively, secondary amplification products may be detected during PCR at the lower temperature points of the cycling protocol (60°–75° C.) with the amplification polymerase serving to stabilize the double-stranded structure of secondary amplification products and maintain a detectable change in FP.

As an alternative to using a signal primer, the amplification primers of any of the foregoing amplification methods may be fluorescently labeled. Double-stranded fluorescently-labeled amplification products are generated from the single-stranded amplification primers with an associated change in FP. Because background will be higher in this embodiment, sensitivity may be reduced as compared to use of a signal primer.

Any fluorescent molecule known in the art for labeling nucleic acids may be used in the methods of the invention, for example, fluorescein and fluorescein derivatives such as 5-(4,6-dichlorotriazin-2-yl) amino fluorescein (5-DTAF); eosin; rhodamines such as Texas Red and tetramethylrhodamine; cyanine dyes such as thiazole orange, oxazole yellow and related dyes described in U.S. Pat. Nos. 4,957,870 and 4,888,867; pyrene; porphyrin dyes such as La Jolla Blue. The fluorescent label should be selected such that its fluorescent lifetime is comparable in magnitude to the correlation time being measured, taking into account that temperature, viscosity, and the size of the oligonucleotide to which the fluorescent dye is conjugated all affect tumbling time. For example, fluorescein (lifetime approximately 4 nanosec.) and LaJolla Blue (lifetime approximately 2 nanosec.) are both useful for correlation times of about 0.1–100 nanosec. If a nucleic acid binding protein is used in conjunction with the fluorescent label, the correlation time is generally increased. For example, correlation time for a free fluorescein label is about 0.2 nanosec. The correlation time increases to about 0.4 nanosec. when the fluorescein label is conjugated to a single stranded oligonucleotide and increases further to about 2 nanosec. when conjugated to a double-stranded oligonucleotide. When FP is enhanced by binding the fluorescein-labeled double-stranded oligonucleotide with a double-stranded DNA binding protein such as EcoRi, the correlation time increases again to about 20 nanosec. La Jolla Blue (Devlin, et al. 1993. Clin. Chem. 39, 1939–1943) is particularly useful for labeling the fluorescent signal primer when biological samples are to be amplified, as this dye absorbs and emits light in the near-infra red spectrum, a region of relatively low background fluorescence with clinical specimens (peak maxima at about 685 nm and 705 nm, respectively). It has also been found that 5-DTAF is superior to fluorescein for FP analysis when used as a label for nucleic acids. This label provides a significantly increased dynamic range as compared to fluorescein and improves the sensitivity of the FP assay.

The fluorescent label is covalently linked or conjugated to the signal primer so as not to interfere with either emission of fluorescence from the label or hybridization of the probe to the target sequence. As FP changes occur when the label is near or involved in a conformational change, the linkage should be in proximity to the site where the conformational change is expected. This is generally at either the 5' end of the signal primer or at an internal site. In general, the label is not linked to the 3' end of the signal primer, as the 3' end must be available for extension by polymerase. A more rigid linkage or "tether", such as one containing double bonds, slows the tumbling time of the fluorescent label and allows measurement of longer correlation times. The fluorescent label is covalently coupled to the signal primer via a linker or "tether" suitable for use in conjugating labels to oligonucleotides, e.g., amino-ethyl, amino-hexyl and amino-propyl linking arms (Applied Biosystems, Clontech, Glen Research, Devlin, et al., supra.). Other amino linkers are described in WO 92/18650. The label may also be conjugated to the oligonucleotide at C5 of pyrimidines or C8 of purines, as generally described by Goodchild, 1990. Bioconj. Chem. 1, 165. Fluorescein may be linked internally by synthesis of an oligonucleotide containing a phosphorothioate, and subsequent reaction with iodoacetamidofluorescein. Methods for linking 5-DTAF to oligonucleotides typically involve reaction of an amino-modified oligonucleotide with 5-DTAF in a $NaHCO_3/Na_2CO_3$ buffer. The labeled oligonucleotide is purified from unreacted excess dye by column chromatography and unlabeled oligonucleotide is removed to produce the final product.

It should be noted that when a change in FP is used for detection of amplification in real-time (i.e., concurrently with conversion of the signal primer to double-stranded form during amplification rather than after completion of the reaction), it is not necessary to "zero" the sample to compensate for background fluorescence as it is for any endpoint measurement. This is because in FP detection a change in polarization or the rate of change in polarization (not the absolute magnitude of the change) indicates a positive result. Lower concentrations of fluorescently labelled signal primer improve detection sensitivity by ensuring that a greater percentage of single-stranded signal primer is converted to double-stranded form for a given concentration of amplified product. However, low signal primer concentrations may result in saturation of the signal primer over a broad range of amplified product levels when endpoint measurements are taken. End-point measurements of FP, taken after completion of the amplification reaction, may therefore not be strictly quantitative with regard to the initial target levels. Monitoring FP in real-time overcomes the problem of signal primer saturation because samples containing higher target levels exhibit more rapid increases in FP values than those containing less target. Of course, the correlation between the rate of FP increase and initial target levels is valid only when comparing samples in which the rate of amplification is essentially identical. For clinical specimens, each of which contains varying levels of amplification inhibitors, the assay may not be strictly quantitative. For example, it may be difficult to differentiate a sample which contains a high amount of initial target and undergoes inefficient amplification from a sample which contains a low amount of initial target but undergoes amplification at a high rate. Nevertheless, real-time monitoring of FP values during amplification provides at least a semi-quantitative estimate of initial target levels. Quantitation may be improved by including an additional target sequence at a known initial concentration as an internal positive control (Walker, et al. 1994. *Nucl. Acids Res.* 22, 2670–2677), or running a sample containing the positive control in parallel. The internal positive control target not only provides an indication of general amplification performance for a sample (ie., a control for false negatives), it also provides a standard for quantitating the initial amount of target in the sample.

EXAMPLE 1

An IS6110 target sequence of *Mycobacterium tuberculosis* was amplified by tSDA, with inclusion of a signal primer for detection of amplification by generation of secondary amplification products. All oligodeoxynucleotides were synthesized using standard techniques and purified by gel electrophoresis. The 5'-fluorescein labeled signal primer was prepared using standard procedures and 6-FAM AMIDITE (Applied Biosystems, Inc.). The signal primer hybridized to nucleotide positions 985–1010 of the IS61 10 element (D. Thierry, et al. 1990. *Nucl. Acids Res.* 18, 188) and had the following sequence:

5'-ATCCGTATGGTGGATAACGTCTTTCA (SEQ ID NO:1)

The amplification and bumper primers were as follows, with the BsoBI recognition sequence shown in bold italics and the IS6 1 10 target binding sequence underlined:

5'-CGATTCCGCTCCAGAC*TTCT CTACT*GAGATCCCCT (SEQ ID NO:2, S$_1$)

5'-ACCGCATCGAATGCAT*CTCTC AAGGCG*TACTCGACC (SEQ ID NO:3, S$_2$)

5'-CGCTGAACCGGAT (SEQ ID NO:4, B$_1$)

5'-TCCACCCGCCAAC (SEQ ID NO:5, B$_2$)

tSDA was performed in 100 μL samples with the final concentrations of reagents as follows: 35 mM K$_2$HPO$_4$ (pH 7.5), 3 mM TRIS-HCl (pH 7.9), 15 mM NaCl, 0.3 mM DTT, 10.5 mM MgCl$_2$, 1.4 mM each dGTP, dATP, TTP and dCTPαS, 0.1 mg/mL bovine serum albumin, 500 ng human placental DNA, 15 nM primer S$_1$, 6 nM primer S$_2$, 5 nM each primers B$_1$ and B$_2$, 320 units BsoBI (New England Biolabs), 8 units Bca (Panvera), 5 nM 5'-fluorescein labeled signal primer and the amounts of *M. tuberculosis* DNA indicated in Table I. The samples were initially prepared in 70 μL of 50 mM K$_2$HPO$_4$ (pH 7.5), 10.7 mM MgCl$_2$, 2 mM each dGTP, dATP, TTP and dCTPαS, 0.14 mg/mL bovine serum albumin, 21.4 nM primer S$_1$, 85.7 nM primer S$_2$, 7.1 mM each primers B$_1$ and B$_2$, and 7.1 nM 5'-fluorescein labeled signal primer. Varying amounts of target were then added to each sample in a 10 μL aliquot of 10 mM TRIS-HCL pH 7.9, 10 mM MgCl$_2$, 50 mM NaCl, 1 mM DTT with 500 ng of human placental DNA. These 80 μL samples were denatured by heating for 2 min. in a boiling water bath and equilibrated for 3 min. at 60° C. for primer annealing. BsoBI and exo⁻ Bca polymerase were diluted together to 16 units/1 μL and 0.4 units/μL, respectively, in 10 mM TRIS-HCl pH 7.9, 10 mM MgCl$_2$, 50 mM NaCl, 1 mM DTT and added in a 20 μL aliquot to each 80 μL SDA sample equilibrated at 60° C. After mixing, SDA was allowed to proceed for 15 min. at 60° C. and was then terminated by addition of 6 μL of 0.5M EDTA. The samples were diluted with 0.9 mL of 55 mM NaCl, 111 mM TRIS-HCl (pH 7.5), 0.7 mM K$_2$HPO$_4$ (pH 7.4), 1.1 mM EDTA, 0.7 mM β-mercaptoethanol, 27 μg/mL bovine serum albumin, 0.02% TRITON X-100, 7% (v/v) glycerol. Fluorescence polarization was measured on an fluorometer specifically designed for fluorescein (Model FPM-1, Jolley Consulting and Research) after equilibration at 37° C. A preparation of an exonuclease deficient Klenow fragment of *E. coli* polymerase I (United States Biochemical) was then added (5 μL of a 5 units/μL stock solution) and fluorescence polarization was recorded a second time at 37° C.

The signal primer exhibited a target amplification-dependent increase in fluorescence polarization as shown in Table I (mP):

TABLE I

| Number of *M. tuberculosis* genomes | | | | |
|---|---|---|---|---|
| 1000 | 100 | 10 | 1 | 0 |
| 114 (154) | 108 (136) | 79 (95) | 62 (68) | 57 (60) |

*values in parentheses are post polymerase addition

Samples containing higher input target exhibited higher polarization values, while the negative control (0 input target) exhibited a polarization value comparable to that of the single-stranded signal primer. Amplification of ten *M. tuberculosis* genomes was clearly detectable over the negative control and amplification of one genome was slightly increased above background.

Upon addition of exo⁻ Klenow polymerase, FP values increased considerably for the amplified samples which contained *M. tuberculosis* DNA, resulting in increased assay sensitivity. This is presumably because binding of the polymerase to the double-stranded secondary amplification product further slows the tumbling time of the fluorescent label on the signal primer. There was essentially no increase in FP with added polymerase in the sample which did not contain the target, demonstrating that there is very little mispriming by the signal primer in tSDA. The higher operating temperature of tSDA also reduces non-specific background amplification to a level which eliminates the need for sequence-specificity in the DNA binding protein. That is, at the completion of tSDA the double-stranded DNA present is predominantly target-specific, allowing use of a double-stranded DNA binding protein which does not specifically bind to the secondary amplification products to enhance the change in FP. Any sequence non-specific double-stranded DNA binding protein should therefore be effective to enhance the change in FP under the conditions of tSDA and other thermophilic amplification reactions.

Evidence of enhancement of the change in FP was evident even before addition of the exo⁻ Klenow polymerase. Similar effects were observed in mock SDA reactions where the signal primer was hybridized to a complementary oligodeoxynucleotide. In the absence of BsoBI and Bca, FP increased from about 55 to 70 mP upon hybridization. Addition of BsoBI and Bca resulted in a hybridization-associated increase in FP to about 125 mP. These results were unexpected because conventional SDA, with FP similarly measured at 37° C., did not show any enhancement in the absence of an additional, sequence-specific double-stranded DNA binding protein. The results of the mock SDA reactions, and the observation of MP values greater than 70 mP prior to addition of polymerase in the high target samples in Table I, suggest that double-stranded DNA binding proteins present in the amplification reaction also serve to enhance the change in FP. Further, fluorescence polarization begins to decrease if tSDA is extended beyond the time of maximum target amplification (generally about 15 min.). This is also the point of the amplification reaction at which non-specific background products begin to increase.

EXAMPLE 2

Endpoint measurements of fluorescence polarization were used to detect amplification of a target sequence in *Chlamydia trachomatis* elementary bodies (EB). EB's of *C. trachomatis* (serovar E) were heated for 15 min. at 95° C. to decrease the infectivity of the sample and to lyse the EB's. This released the DNA for amplification. Serial dilutions of the lysate were made with 10 ng/µL human placental DNA in water. The $S_1$, $S_2$, $B_1$ and $B_2$ primers were synthesized using phosphoramidite chemistry on an Applied Biosystems 380B synthesizer as recommended by the manufacturer. The oligonucleotides were ammonium hydroxide deprotected at 50° C. for 16 hrs. and purified by gel electrophoresis using conventional methods. The signal primer was synthesized with a six carbon AMINOLINK (ABI) on the 5' phosphate. This oligonucleotide was conjugated to 5-DTAF at its 5' end as follows. The amino oligonucleotide (56 µL of a 150 µM solution) was mixed with 60 µL of 10 $NaHCO_3/Na_2CO_3$ buffer (25 mM, pH 9). To this solution was added 10 µL of 40 mM 5-DTAF in DMF. The reaction was allowed to incubate at 37° C. for 72 hrs. in the dark. The labeled oligonucleotide was first purified from excess unreacted dye by column chromatography on a NAP-5 column (Pharmacia) equilibrated with 25 mM $NaHCO_3/Na_2CO_3$ buffer. Several 0.5 mL fractions were collected and the labeled oligonucleotide was found in Fraction 2. Fraction 2 was then further purified to separate labeled from unlabeled oligonucleotide using an Oligonucleotide Purification Cartridge (OPN, ABI) and conventional protocols. The final fraction was assayed for spectral purity on an HP 89532A spectrophotometer, scanning 240–600 nm. Optical densities were: $A_{260}$ 0.11273, $A_{494}$ 0.0215, $A_{260/280}$ 1.62, $A_{260/494}$ 5.25.

For the endpoint measurements, tSDA was performed in a 50 µL volume containing 5 mM $MgCl_2$, 0.2 mM each dGTP, dATP, TTP, 1.4 mM dCTPαS, 20 µg/mL non-acetylated bovine serum albumin, 1 ng/µL human placental DNA, 40 mM $K_2HPO_4$ pH 7.6, 5% (v/v) glycerol, 3% (v/v) DMSO, 750 nM primer $S_1$, 188 mM primer $S_2$, 75 mM primers $B_1$ and $B_2$, 10 nM signal primer, 3.2 units/µL BsoBI, 0.25 units/µL exonuclease deficient Bst DNA polymerase (Molecular Biology Resources) and varying amounts of Chlamydia EB's. To facilitate signal primer hybridization to the target prior to hybridization of $S_2$, in this example the $S_2$ primer was in four-fold lower concentration than the $S_1$ primer and in 18.75-fold higher concentration than the signal primer. Prior to addition of BsoBI, Bst polymerase, BSA and $MgCl_2$, 5 µL of the target preparation was added and the reactions were heated at 95° C. for 2 min. to denature the target DNA. This was followed by equilibration for 5 min. at 53.5° C. to anneal the primers. Following addition of 10 µL of enzyme mix containing 5 µL 50 mM $MgCl_2$, 1 µL BSA (1 mg/mL), 1 µL Bst polymerase (25 units/µL), 1 µL BsoBI (160 units/µL) and 2 µL 1X NEB2 (10 mM TRIS-HCl pH 7.9, 50 mM NaCl, 10 mM $MgCl_2$, 1 mM dithiothreitol—New England BioLabs), the reactions were incubated at 53.5° C. for 30 min. for amplification. An aliquot of the amplification reaction (45 µL) was added to 1 mL FP buffer (100 mM TRIS pH7.5, 1 mM EDTA, 44 mM NaCl, 0.5 mM βME, 20 µg/mL BSA, 0.015% TRITON-X 100, 5% glycerol) at 37° C. and read in an FPM-1 fluorometer using the following settings: read mode—static; single blank, blank delay and sample delay—10 sec.; PMT voltage —80; FP Factor—1.0020; lamp feedback—off, number read cycles—1.

Figure 1:
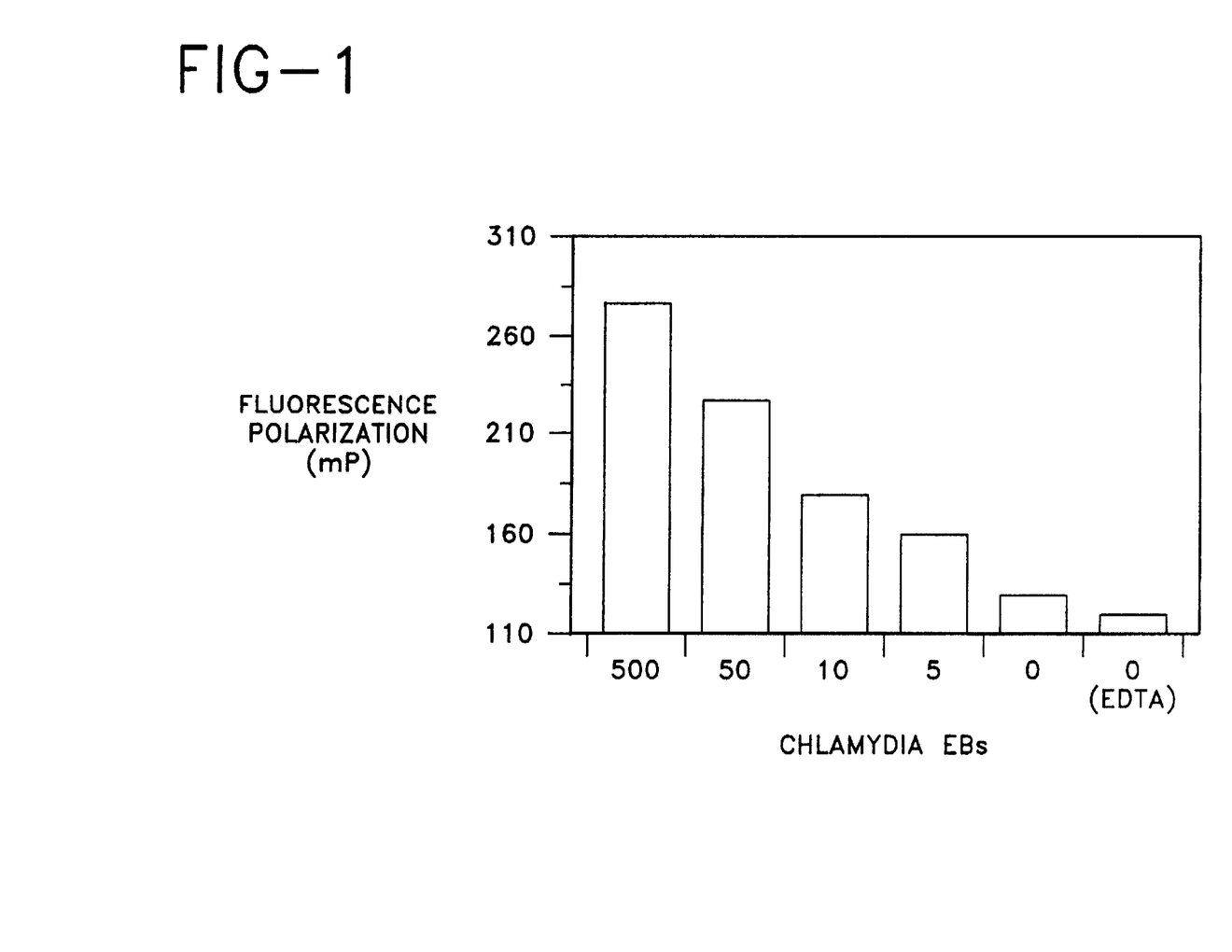
FIG. 1 is a histogram plot illustrating the sensitivity of the methods of the invention for a *Chlamydia trachomatis* target sequence.

The endpoint measurements were used to evaluate the sensitivity of the DTAF system, detecting amplification of 500, 50, 10, 5, and 0 EB's. Amplification of five Chlamydia EB's could easily be seen above background (FIG. 1). Two negative control reactions were run—one without target DNA and one in which SDA was inhibited by EDTA. The reaction without target showed a slight rise in mP due to contamination with target or amplicons from previous reactions at a level less than five EB's. Contamination was possible in this system because the endpoint assay was not a closed-tube homogeneous assay. As endpoint FP measurements reflect the amount of signal primer converted to the double-stranded form, at higher input target levels the results are non-quantitative because essentially 100% of the signal primer will be converted. While more signal primer could be added to the reaction to quantitate higher target concentrations, this would compromise sensitivity at lower concentrations of target where more signal primer would have to be converted to produce a detectable increase in the average correlation time. Again, enhanced FP values (greater than about 230 mP using a 5-DTAF end-label) were observed in samples containing target, indicating that under thermophilic amplification conditions sequence non-specific double-stranded DNA binding proteins present in the amplification reaction contribute to enhanced AmP by binding to secondary amplification products.

EXAMPLE 3 tSDA reactions for real-time monitoring were performed as in Example 2 in 1 mL volumes with 100 µL of the target preparation. There were four reactions (containing either $10^6$, $10^4$, $10^2$ or 0 EB's) to evaluate the quantitative aspects of the assay. The negative SDA sample contained 10 mM EDTA and served as a fluorescence polarization control. After denaturing the target at 95° C. for 5 min. the samples (800 µL) were transferred to a 10 mm×45 mm cuvette in an SLM 8100 spectrofluorometer (Milton-Roy) and equilibrated at 53.5° C. for 10 min. using water circulating temperature control. Amplification was initiated by addition of 200 µL enzyme mix and fluorescence polarization was monitored every 2 min. for a total of 45 min. The SLM 8100 spectrofluorometer has four cuvette chambers which can be read sequentially to allow all samples to be analyzed at the same time.

The polymerase used in the amplification reaction unexpectedly made it possible to perform real time detection in a closed-tube format at the elevated temperature. End fraying and/or breathing in the double-stranded secondary amplification products was apparently reduced or eliminated by binding of this double-stranded DNA binding protein, resulting in an increase of FP to approximately 220 mP with single- to double-stranded conversion of the signal primer. Preliminary experiments had indicated that there would be no difference in FP for the single- to double-stranded conversion due to inicreased single-strandedness near the label at higher temperatures. Although the restriction endonuclease in the amplification reaction is also a double-stranded DNA binding protein, Applicants believe its contribution to stabilization of the duplex at higher temperatures is minimal, as no binding was detected in the absence of a recognition site for the restriction endonuclease in the secondary amplification product.

Figure 2:
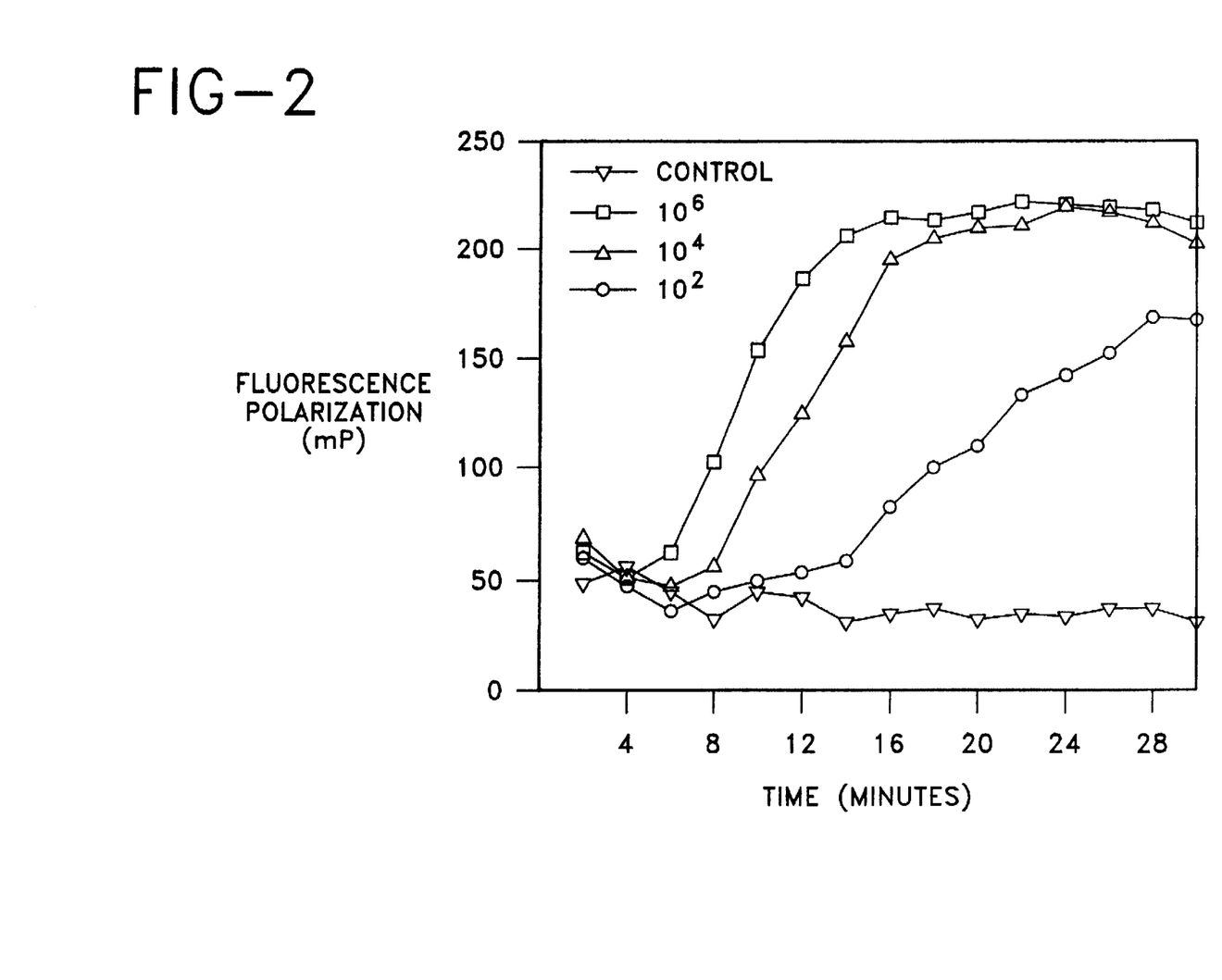
FIG. 2 is a graph illustrating real-time detection and quantitation of varying amounts of a *Chlamydia trachomatis* target using the methods of the invention.

FIG. 2 shows the results for the first 30 min. of real-time detection of target amplification. The reactions containing $10^6$ and $10^4$ EB's plateaued at about 20 min., with mP values of about 200–220. However, a quantitative difference could be seen at all target levels during real-time detection, as samples containing higher initial levels of target showed an increase in FP sooner than those containing lower initial target levels. As shown in FIG. 2, $10^6$ EB's were detectable by an increase in FP in about 8 min., $10^4$ EB's were detectable by an increase in FP in about 10 min. and $10^2$ EB's were detectable by an increase in FP in about 16 min. Real-time detection therefore overcomes the limitations of endpoint analysis when it is desired to quantitate the initial amount of target present. In controlled experiments such as this one, all samples are expected to exhibit essentially the same rate of SDA and the assay is quantitative. However, clinical samples may contain inhibitors of amplification which decrease the rate of amplification relative to controls. For real-time quantitation in such samples, an internal control sequence at a known initial concentration could be co-amplified in the clinical specimen using a different fluorophore, or in a parallel reaction using the same fluorophore. The effect of the clinical sample on quantitation of the internal control could then be applied to accurately quantify the clinical target.

What is claimed is:

1. A method for detecting amplification of a nucleic acid target sequence comprising:

a) amplifying the target sequence in an amplification reaction at about 45°–75° C., the amplification reaction comprising a strand displacing polymerase and a fluorescently-labeled single-stranded signal primer which hybridizes to a first strand of the target sequence downstream of a first amplification primer, thereby producing a signal primer extension product which is displaced from the first strand of the target sequence by extension of the first amplification primer,    b) hybridizing a second amplification primer to the displaced signal primer extension product and extending the second amplification primer, thereby producing a fluorescently-labeled double-stranded secondary amplification product, and;

c) detecting production of the double-stranded secondary amplification product by fluorescence polarization in the presence of a sequence-nonspecific double-stranded DNA binding protein as an indication of target sequence amplification.

2. The method of claim 1 wherein the amplification reaction is thermophilic Strand Displacement Amplification.

3. The method of claim 2 wherein the strand displacing polymerase is Bca or Bst.

4. The method of claim 2 wherein the target sequence is amplified at about 50°–60° C.

5. The method of claim 1 wherein the amplification reaction is the Polymerase Chain Reaction (PCR).

6. The method of claim 1 wherein the signal primer is fluorescently-labeled with fluorescein or 5-(4,6-dichlorotriazin-2-yl) amino fluorescein.

7. The method of claim 1 wherein a second double-stranded DNA binding protein is added after target amplification to enhance fluorescence polarization values.

8. The method of claim 7 wherein the second double-stranded DNA binding protein is a second polymerase.

9. The method of claim 1 wherein fluorescence polarization is detected at an endpoint.

10. The method of claim 9 wherein fluorescence polarization is detected at a temperature below about 45° C.

11. The method of claim 1 wherein fluorescence polarization is measured concurrently with target amplification.

12. The method of claim 11 further comprising using fluorescence polarization values to quantitate an initial amount of the target sequence.

13. The method of claim 12 wherein the initial amount of the target sequence is quantitated by analyzing a rate of increase in fluorescence polarization values.

14. The method of claim 1 wherein fluorescence polarization is detected at about 45°–75° C.

15. The method of claim 14 wherein fluorescence polarization is detected at an endpoint.

16. The method of claim 14 wherein fluorescence polarization is detected concurrently with target amplification.

17. The method of claim 1 wherein the target sequence is an M. tuberculosis target sequence.

18. The method of claim 1 wherein the target sequence is a C. trachomatis target sequence.

19. A method for detecting amplification of a nucleic acid target sequence comprising:

a) amplifying the target sequence in a thermophilic Strand Displacement Amplification (tSDA) reaction at about 45° C.–65° C., the tSDA reaction comprising a strand displacing polymerase and a fluorescently-labeled single-stranded signal primer which hybridizes to a first strand of the target sequence downstream of a first amplification primer, thereby producing a signal primer extension product which is displaced from the first strand of the target sequence by extension of the first amplification primer,    b) hybridizing a second amplification primer to the displaced signal primer extension product and extending the second amplification primer, thereby producing a fluorescently-labeled double-stranded secondary amplification product, and;

c) detecting production of the secondary amplification product by fluorescence polarization in the presence of a sequence-nonspecific double-stranded DNA binding protein as an indication of target sequence amplification.

20. The method of claim 1 wherein the sequence-nonspecific DNA binding protein is the strand displacing polymerase.

* * * * *